(12) United States Patent
Pinkos et al.

(10) Patent No.: US 7,790,930 B2
(45) Date of Patent: Sep. 7, 2010

(54) METHOD FOR PURIFYING CYCLIC KETONES

(75) Inventors: Rolf Pinkos, Bad Dürkheim (DE); Gerd Tebben, Mannheim (DE); Christian Müller, Mannheim (DE); Harald Rust, Neustadt (DE)

(73) Assignee: BASF SE (DE)

( * ) Notice: Subject to any disclaimer, the term of this patent is extended or adjusted under 35 U.S.C. 154(b) by 0 days.

(21) Appl. No.: 12/306,815

(22) PCT Filed: Jun. 27, 2007

(86) PCT No.: PCT/EP2007/056393

§ 371 (c)(1), (2), (4) Date: Dec. 29, 2008

(87) PCT Pub. No.: WO2008/000754

PCT Pub. Date: Jan. 3, 2008

(65) Prior Publication Data

US 2009/0318733 A1   Dec. 24, 2009

(30) Foreign Application Priority Data

Jun. 29, 2006   (EP) .................................. 06116260

(51) Int. Cl.
*C07C 45/27* (2006.01)
(52) U.S. Cl. .................................................. 568/365
(58) Field of Classification Search .................. 568/365
See application file for complete search history.

(56) References Cited

U.S. PATENT DOCUMENTS

| 316,917 | A | 4/1885 | Russell |
|---|---|---|---|
| 3,804,914 | A | 4/1974 | Fahey |
| 5,128,296 | A | 7/1992 | Matson et al. |
| 5,177,278 | A | 1/1993 | Sanchez |
| 5,180,870 | A | 1/1993 | Paciello |
| 5,210,349 | A | 5/1993 | Matson et al. |
| 5,321,176 | A | 6/1994 | Sanchez |
| 6,335,472 | B1 | 1/2002 | Matsuzaki et al. |
| 6,649,757 | B2 | 11/2003 | Kuroda et al. |
| 7,153,114 | B2 | 12/2006 | Snyder et al. |
| 2006/0281952 | A1 | 12/2006 | Teles et al. |
| 2008/0275276 | A1 | 11/2008 | Teles et al. |

FOREIGN PATENT DOCUMENTS

| DE | 1 518 566 | 10/1969 |
|---|---|---|
| DE | 1518566 | 10/1969 |
| DE | 2519817 A1 | 11/1976 |
| DE | 103 44 594 A | 5/2005 |
| DE | 103 44 595 | 5/2005 |
| DE | 10344594 A1 | 5/2005 |
| DE | 10344595 A1 | 5/2005 |
| EP | 0285420 A1 | 10/1988 |
| EP | 1 018 498 A2 | 7/2000 |
| EP | 1018498 A2 | 7/2000 |
| EP | 1 329 448 | 7/2003 |
| EP | 1329448 A1 | 7/2003 |
| EP | 1 477 219 A1 | 11/2004 |
| EP | 1477219 A1 | 11/2004 |
| GB | 1145476 | 3/1969 |
| GB | 1551741 | 8/1979 |
| JP | 50-31145 B | 10/1975 |
| WO | WO-02/12156 A1 | 2/2002 |

OTHER PUBLICATIONS

U.S. Appl. No. 12/306,841, filed Dec. 29, 2008.
U.S. Appl. No. 12/306,827, filed Dec. 29, 2008.
U.S. Appl. No. 12/306,807, filed Dec. 29, 2008.
Schiffer, Thomas, et al., "Cyclodoecanol, Cyclododecanone, and Laurolactam" Wiley-VCH Verlag GmbH & Co. KGaA, Weinheim, pp. 1-5, (2005).
Schiffer, Thomas, et al., "Cyclododecatriene, Cyclooctadiene, and 4-Vinylcyclohexene" Wiley-VCH GmbH & Co. KGaA, Weinheim, pp. 1-4, (2005).
Weber, H., et al., "Zur Bildungsweise Von cis, trans, trans-Cyclododecatrien-(1.5.9) Mittel Titanhaltiger Ziegler-Katalysatoren" Herrn Prof. Dr. Clemens Schopf zum 65. Geburtstag gewidmet, pp. 10-20, Mar. 11, 1964.
Fahey, Daryl R., "Selective Hyrdrogenation of 1,5,9-Cyclododecatriene to Cyclododecene Catalyzed by Ruthenium Complexes" The Journal of Organic Chemistry, vol. 38, No. 1, pp. 80-87 (1973).
Muller, Eugen, et al., "Methoden Der organischen Chemie" Georg Thieme Verlag Stuttgart, New York, vol. 17, No. 2, pp. 16-28 (1980).
Muller, Eugen, et al., "methoden Der Organischen Chemie" Georg Thieme Verlag Stuttgart, New York, vol. 28, No. 2, pp. 25-67 (1980).
Asahi Chemical Ind KK, "Cycloalkanones prepn. from cyclalkanes—by dehydrogenating its air-oxidn. prods contg. cycloalkanols" p. 210, (Dec. 25, 1970).

*Primary Examiner*—Sikarl A Witherspoon
(74) *Attorney, Agent, or Firm*—Connolly Bove Lodge & Hutz LLP

(57) ABSTRACT

The present invention relates to a process for purifying a composition (I) comprising at least one cyclic ketone having from 7 to 16 carbon atoms, which comprises thermal treatment of the composition (I) with a catalyst comprising at least one transition metal and further purification by means of a process selected from the group consisting of distillation, extraction and crystallization. Furthermore, the present invention relates to a process for preparing cyclododecanone, which comprises such a purification, and the use of at least one catalyst comprising at least one transition metal for purifying a composition (I) comprising at least one cyclic ketone having from 7 to 16 carbon atoms by thermal treatment of the composition (I) with a catalyst comprising at least one transition metal.

18 Claims, No Drawings

METHOD FOR PURIFYING CYCLIC KETONES

CROSS-REFERENCE TO RELATED APPLICATIONS

This application is a national stage application (under 35 U.S.C. §371) of PCT/EP2007/056393, filed Jun. 27, 2007, which claims benefit of European application 06116260.8, filed Jun. 29, 2006.

BACKGROUND OF THE INVENTION

The present invention relates to a process for purifying a composition (I) comprising at least one cyclic ketone having from 7 to 16 carbon atoms, which comprises thermal treatment of the composition (I) with at least one catalyst comprising at least one transition metal and further purification by means of a process selected from the group consisting of distillation, extraction and crystallization. The present invention further relates to a process for preparing cyclododecanone, which comprises such a purification, and the use of at least one catalyst comprising at least one transition metal for purifying a composition (I) comprising at least one cyclic ketone having from 7 to 16 carbon atoms by thermal treatment of the composition (I) with the catalyst comprising at least one transition metal.

Cyclic ketones are required in high purity for various applications. Due to the production process, cyclic ketones frequently comprise impurities, for example impurities having oxygen-comprising groups which can be removed only with difficulty by means of conventional purification processes such as distillation or crystallization. Conventional purification processes for such separation problems are therefore complicated and costly.

Thus, for example, cyclododecanone is an important intermediate for the preparation of, for example, laurinlactam, dedecanedicarboxylic acid and polyamides derived therefrom, for example Nylon 12 or Nylon 6.12.

Cyclododecanone is prepared, for example, by air oxidation of cyclododecane in the presence of boric acid to form cyclododecylborate, hydrolysis of the borate to form cyclododecanol and subsequently dehydrogenation of the cyclododecanol. Cyclododecane itself is obtained by full hydrogenation of cyclododecatriene. A description of this industrial process for the synthesis of cyclododecanone may be found, inter alia, in T. Schiffer, G. Oenbrink, "Cyclododecanol, Cyclododecanone and Laurolactam" in Ullmann's Encyclopedia of Industrial Chemistry, 6th Edition, 2000, Electronic Release, Wiley VCH.

A further process starts out from the epoxidation of cyclododecatriene, with cyclododecanone being obtained from the epoxide by hydrogenation and rearrangement. Such processes are disclosed, for example, in EP 1 018 498 A2. DE 103 44 595 A and DE 103 44 594 A describe processes for preparing cyclododecanone in which oxidation with dinitrogen monoxide is carried out in one process step.

In all processes, the purity of the crude products is not sufficient for some applications without additional purification. Organic compounds having oxygen-comprising groups in particular are frequently comprised in the products obtained in unacceptably large amounts. In these cases, a very complicated purification, for example by multistage distillation and/or crystallization, is therefore necessary.

BRIEF SUMMARY OF THE INVENTION

It was therefore an object of the present invention to provide a process by means of which cyclic ketones can be obtained in high purity in a simple manner and with a small outlay.

A further object of the present invention was to provide a purification process by means of which oxygen-comprising organic compounds in particular can be separated off from the cyclic ketones.

A further object of the present invention was to provide a purification process for cyclic ketones which can readily be combined with known processes for preparing cyclic ketones.

According to the invention, this object is achieved by a process for purifying a composition (I) comprising at least one cyclic ketone having from 7 to 16 carbon atoms, which comprises at least the steps
(i) thermal treatment of the composition (I) with at least one catalyst comprising at least one transition metal,
(ii) further purification by means of a process selected from the group consisting of distillation, extraction and crystallization.

DETAILED DESCRIPTION OF THE INVENTION

The process of the invention enables cyclic ketones to be obtained in a purity of, for example, >99.5%. The process of the invention can in particular be carried out subsequent to a basically known process for preparing a cyclic ketone having from 7 to 16 carbon atoms. The process of the invention can in this way easily be combined with existing plants, so that costly modifications are not necessary. Furthermore, the process of the invention offers the opportunity of increasing the yield of cyclic ketone, since the treatment with a catalyst comprising at least one transition metal is generally very selective and less product is therefore lost in the subsequent purification by distillation or crystallization.

According to the invention, catalysts based on transition elements having atomic numbers of from 21 to 30, 39 to 48 and 57 to 80 are particularly suitable.

For the purposes of the present patent application, "treatment" means contacting of the composition (I) with at least one catalyst comprising at least one transition metal. In step (i) according to the invention, the composition (I) is treated thermally with a catalyst comprising at least one transition metal.

The process of the invention comprises the steps (i) and (ii). In step (i), the composition (I) is treated thermally with a catalyst comprising at least one transition metal. In step (ii), the composition (I) which has been treated in this way is purified further by distillation, extraction and/or crystallization. Here, the distillation, extraction and/or crystallization can be carried out by all customary methods known to those skilled in the art.

Suitable solvents for the crystallization in step (ii) are, for example, alcohols, ethers, hydrocarbons, aromatic hydrocarbons, ketones, preferably toluene, xylene, methanol, ethanol, propanol, butanol, acetone, diethyl ketone or methyl tert-butyl ether. According to the invention, it is likewise possible for no solvent to be used but instead a melt crystallization to be carried out.

The purification by distillation can be carried out in one or more columns. Pressures of from 1 to 2000 mbar are preferably employed here. Particularly in the case of cyclic ketones having more than 8 carbon atoms, pressures in the range from 5 to 500 mbar are preferred and pressures in the range from 10 to 200 mbar are particularly preferred. The temperatures (temperature at the bottom) are from 100 to 300° C. The temperature in the purification by distillation is preferably from 130 to 250° C., particularly preferably from 150 to 220° C.

In a preferred embodiment of the invention, the purification by distillation is carried out at a pressure of from 1 to 2000 mbar, preferably from 5 to 500 mbar, particularly preferably from 10 to 200 mbar, and a temperature at the bottom of from 100 to 300° C., preferably from 130 to 250° C., particularly preferably from 150 to 220° C.

If only one column is used in the purification by distillation, the desired product is preferably obtained via a side offtake. According to the invention, it is possible to obtain the desired product in liquid or gaseous form. High boilers are preferably separated off at the bottom, while low boilers are preferably separated off at the top. If two columns are used, the desired product together with high boilers preferably goes via the bottom to the second column from which it can then be obtained at the top or once again as a side offtake stream. Dividing wall columns can also be used according to the invention.

According to the invention, it is also possible for further treatments to be carried out between the individual steps of the process. In particular, it is possible according to the invention to separate off the catalyst comprising at least one transition metal after step (i), particularly when the catalyst is present as a homogeneous solution or as a suspension.

Before the distillation, extraction or crystallization in step (ii), it can be advantageous to remove the catalyst from the treated composition (I). In the case of heterogeneous catalysts, this can be achieved, for example, by filtration, while in the case of homogeneous catalysts, possibilities are, for example, extraction, for example with water, or distillation, with the catalyst preferably being separated off at the bottom. After the separation, the catalyst can advantageously be reused in step (i). It is also possible, according to the invention, for the catalyst to be subjected to an intermediate treatment, for example a purification or regeneration, after it has been separated off and before it is reused in step (i).

In a preferred embodiment, the present invention therefore also provides a process as described above for purifying a composition (I) comprising at least one cyclic ketone having from 7 to 16 carbon atoms, wherein the catalyst is separated off after step (i) and, if appropriate, is subsequently reused in step (i).

The treatment with a catalyst comprising at least one transition metal is preferably carried out at temperatures of from 30 to 350° C., for example from 60 to 350° C., in particular from 100 to 270° C., particularly preferably from 130 to 260° C.

In a further embodiment, the present invention therefore also provides a process as described above for purifying a composition (I) comprising at least one cyclic ketone having from 7 to 16 carbon atoms, wherein the treatment in step (i) is carried out at a temperature of from 60 to 350° C.

It has surprisingly been found that in the treatment of compositions comprising at least one cyclic ketone having from 7 to 16 carbon atoms with a catalyst comprising at least one transition metal, cyclic ketones can be obtained in high yields in purities of above 99.5% in a subsequent further purification, for example by means of distillation, extraction and/or crystallization. The cyclic ketone itself is not attacked or attacked only insignificantly. According to the invention, the compounds separated off are, in particular, alcohols, aldehydes and epoxides.

Based on the cyclic ketone comprised in the composition, less than 10% of the ketone, preferably less than 5%, in particular less than 3%, are lost according to the invention.

The treatment in step (i) can be carried out either in the gas phase or in the liquid phase. The pressure can be set within a wide range. It can be, for example, in the range from 0.001 to 300 bar, preferably from 0.01 to 200 bar, particularly preferably from 0.1 to 100 bar. According to the invention, preference is given to a pressure at which any low boilers formed can be removed from the system by distillation, i.e. at a pressure of, for example, from 0.25 to 70 bar, preferably from 0.35 to 50 bar, particularly preferably from 0.5 to 30 bar.

The treatment in step (i) can be carried out discontinuously or continuously, with a continuous treatment being preferred. The residence times are, for example, from 0.1 to 50 hours, preferably from 0.2 to 24 hours, for example from 0.5 to 15 hours, in particular from 1 hour to 19 hours, particularly preferably from 1.5 to 10 hours.

In a further embodiment, the present invention therefore also provides a process as described above for purifying a composition (1) comprising at least one cyclic ketone having from 7 to 16 carbon atoms, wherein the treatment in step (i) is carried out for a time of from 0.1 to 50 hours.

The catalysts used according to the invention comprise at least one transition metal; it is also possible to use catalysts comprising two or more transition metals or mixtures of two or more catalysts comprising at least one transition metal. The catalysts used can be homogeneously dissolved or be heterogeneous. Heterogeneous catalysts can, according to the invention, be suspended or present as a fixed bed.

In a further embodiment, the present invention therefore also provides a process as described above for purifying a composition (I) comprising at least one cyclic ketone having from 7 to 16 carbon atoms, wherein the catalyst is present in homogeneously dissolved form or heterogeneous form.

As catalyst comprising at least one transition metal, it is possible to use all customary catalysts for the purposes of the present invention. Possible transition metals are in principle all transition metals known to those skilled in the art.

The homogeneously soluble catalysts used according to the invention are described, for example, in Houben-Weyl, Methoden der Organischen Chemie, volume IV/1c, pages 45 to 67, Thieme Verlag Stuttgart, 1980.

Preferred homogeneous catalysts comprise Ru, Rh and/or Pd as transition metal. Particular preference is given to Ru.

The content of homogeneously soluble catalyst is generally from 0.001 to 1% by weight, based on the cyclic ketone. Preference is given to using a homogeneously soluble catalyst in an amount of from 0.005 to 0.5% by weight, particularly preferably from 0.01 to 0.1% by weight.

In a preferred embodiment of the present invention, a homogeneously soluble catalyst is used in an amount of from 0.01 to 0.1% by weight.

After the cyclic ketone has been separated off by distillation, the catalyst is preferably recirculated at least partly to the treatment step (i).

Heterogeneous catalysts which are suitable for the purposes of the invention are described, for example, in Houben-Weyl, Methoden der Organischen Chemie, volume IV/1c, pages 16 to 26, Thieme Verlag Stuttgart, 1980. They comprise at least one transition metal. Preferred transition metals are Ni, Cu, Pd, Ru, Ir, Pt, Co and/or Rh. Particular preference is given to Pd, Ru, Pt, and very particular preference is given to Ru and Pd.

The heterogeneous catalysts can be used in suspended form or preferably as a fixed bed. The catalysts comprising at least one transition metal can comprise the transition metal as element or in the form of a chemical compound, for example as oxide. Mixtures of various transition metals can comprise the elements or their compounds as mixtures or as alloys. It is also possible to use elements which are not transition metals as catalyst component, either as elements or compounds, for example in Raney catalysts in which, for example, Al or aluminum oxide are used together with, preferably, Ni, Cu or Ru.

Further catalysts which are suitable for the purposes of the invention are, for example, Ru on aluminum oxide, silicon oxide, titanium oxide, zirconium oxide, barium oxide, calcium oxide, Ru on activated carbon, Pd on aluminum oxide, silicon oxide, titanium oxide, zirconium oxide, barium oxide, calcium oxide, Pd on activated carbon, Pt on aluminum oxide, silicon oxide, titanium oxide, zirconium oxide, barium oxide, calcium oxide or Pt on activated carbon. Mixtures or compounds of various materials, for example clay minerals or zeolites, can also be used as support materials.

The catalyst used in the hydrogenation is also suitable according to the invention.

The catalysts comprising at least one transition metal can, according to the invention, also have been applied to a support. These supports are, for example, metal-oxidic, basic, neutral or acidic solids which, according to the invention, may have been treated with, for example, mineral acids such as phosphoric acid or sulfuric acid to increase the acid strength. Preference is given to oxides or mixed oxides of B, Al, Si, Sn, Ti, Cr, Zr, Fe and Zn, which may comprise further constituents. Examples of suitable supports are zirconium oxide, titanium oxide, aluminum oxide, silicon oxide and combinations thereof e.g. aluminosilicates, such as zeolites. For example, it is possible to use sheet silicates or natural clay minerals.

If the process of the invention is carried out batchwise using heterogeneous catalysts, use is generally made of from 0.1 to 50% by weight of catalyst, based on the cyclic ketone. Preference is given to using a heterogeneous catalyst in an amount of from 0.5 to 20% by weight, particularly preferably from 1 to 10% by weight.

If the process is carried out continuously using a heterogeneous catalyst, preference is given to setting a throughput over the catalyst, i.e. the space velocity over the heterogeneous catalyst, of from 0.01 to 10 kg of cyclic ketone/liter of catalyst×h. In particular, a space velocity over the catalyst of from 0.05 to 2 kg of cyclic ketone/liter of catalyst×h, particularly preferably from 0.1 to 1 kg of cyclic ketone/liter of catalyst×h, is set.

In a preferred embodiment, the present invention therefore provides a process as described above, wherein a heterogeneous catalyst is used at a space velocity over the catalyst of from 0.01 to 10 kg of cyclic ketone/liter of catalyst×h.

According to the invention, it is possible for the catalyst comprising at least one transition metal to be separated off in step (ii). However, it is likewise possible within the scope of the present invention for the catalyst to be separated off after step (i) and before step (ii). Possible methods of separating it off are, for example, distillation, extraction, precipitation or crystallization.

In a further embodiment, the present invention therefore also provides a process as described above, wherein the catalyst comprising at least one transition metal is at least partly separated off after step (i) and before step (ii).

According to the invention, the composition (I) comprises at least one cyclic ketone having from 7 to 16 carbon atoms.

The at least one cyclic ketone is preferably a ketone having from 8 to 14 carbon atoms, particularly preferably from 9 to 12 carbon atoms, for example cyclodecanone or cyclododecanone.

In a further embodiment, the present invention therefore also provides a process as described above for purifying a composition (I) comprising at least one cyclic ketone having from 7 to 16 carbon atoms, wherein the cyclic ketone is cyclododecanone.

The composition (I) usually comprises the cyclic ketone in an amount of more than 80% by weight, preferably from 85 to 99% by weight, in particular from 88 to 99.9% by weight, particularly preferably from 90 to 99.6% by weight, more preferably from 92 to 99.0% by weight. In addition to the cyclic ketone, the composition (I) usually comprises further compounds, in particular organic compounds, preferably ones having oxygen-comprising groups, for example alcohols, aldehydes or epoxides, which are preferably separated off by means of the purification process of the invention. Here, the organic compounds can have, in particular, the same number of carbon atoms as the cyclic ketone comprised in the composition (I).

Before carrying out the purification according to the invention, the secondary components are comprised in the composition (I) in an amount of, in particular, less than 20% by weight, in particular less than 15% by weight, particularly preferably less than 12% by weight. For example, the secondary components are comprised in an amount of from 0.001 to 10% by weight, in particular from 0.1 to 9% by weight, preferably from 0.5 to 5% by weight, particularly preferably from 1 to 4% by weight.

In a further embodiment, the present invention therefore also provides a process as described above for purifying a composition (I) comprising at least one cyclic ketone having from 7 to 16 carbon atoms, wherein the composition (I) comprises at least one further oxygen-comprising organic compound in addition to the at least one cyclic ketone.

A cyclic ketone is obtained in a purity of >95%, for example >98%, in particular >99%, determined by gas-chromatographic methods, by means of the purification process of the invention. The cyclic ketone is preferably obtained in a purity of >99.5%, more preferably >99.8%, particularly preferably >99.9%.

The composition (I) comprising at least one cyclic ketone having from 7 to 16 carbon atoms can be obtained via all customary production processes for such cyclic ketones.

According to a further aspect, the present invention provides a process for preparing a cyclic ketone having from 7 to 16 carbon atoms, which comprises at least the steps
  (a) preparation of a composition (I) comprising at least one cyclic ketone having from 7 to 16 carbon atoms,
  (b) purification of the composition (1), which comprises at least the steps
    (i) thermal treatment of the composition (I) with at least one catalyst comprising at least one transition metal,
    (ii) further purification by means of a process selected from the group consisting of distillation, extraction and crystallization.

If, according to a preferred embodiment, the composition (I) comprises cyclododecanone as cyclic ketone, this can be obtained via all production processes known to those skilled in the art for cyclododecanone.

In a further embodiment, the present invention provides a process for preparing cyclododecanone, which comprises at least the steps
  (a) preparation of a composition (I') comprising at least cyclododecanone, (b) purification of the composition (I'), which comprises at least the steps
  (i) thermal treatment of the composition (I') with a catalyst comprising at least one transition metal,
  (ii) further purification by means of a process selected from the group consisting of distillation, extraction and crystallization.

The preparation of the composition (I') in step (a) can be carried out in one or more stages, i.e. the composition (I') is obtained by a single-stage or multistage synthesis of cyclododecanone. In step (b), the composition (I') obtained in this way is purified.

For example, cyclododecanone can be obtained by air oxidation of cyclododecane in the presence of boric acid or Co salts. Cyclododecanone can also be prepared, for example, by hydrogenation of cyclododecadienone, by oxidation of cyclododecane, by oxidation of cyclododecene by means of dinitrogen monoxide or by hydrogenation of cyclododecatriene epoxide. Cyclododecanone can also be obtained, for example, by reaction of cyclododecene. According to the invention, all processes known to those skilled in the art for preparing cyclodedanone are suitable in principle.

In a further embodiment, the present invention also provides a process as described above for preparing cyclododecanone, wherein step (a) comprises at least the steps
  (a1) trimerization of butadiene to form cyclododecatriene,
  (a2) oxidation of cyclododecatriene to form cyclododecadienone,
  (a3) hydrogenation of cyclododecadienone to form cyclododecanone.

According to the invention, cyclododecanone is preferably obtained by hydrogenation as per step (a3) of cyclododecadienone which has in turn been obtained by oxidation of a cyclododecatriene, preferably by means of dinitrogen monoxide, as per step (a2). According to the invention, cyclododecatriene is preferably obtained by trimerization of butadiene as per step (a1). Further treatments, for example purification steps, can, according to the invention, be carried out between steps (a1), (a2) and (a3).

According to the invention, no treatment of the composition obtained in step (a2) with at least one base is carried out between steps (a2) and (a3). In this context, treatment is a contacting of the composition with at least one base.

Step (a1) comprises the trimerization of butadiene. 1,5,9-cyclododecatriene can be prepared, for example, by trimerization of pure 13-butadiene as described, for example, in T. Schiffer, G. Oenbrink, "Cyclododecatriene, Cyclooctadiene, and 4-Vinylcyclohexene", Ullmann's Encyclopedia of Industrial Chemistry, 6th Edition (2000), Electronic Release, Wiley VCH. This process forms, for example in the trimerization in the presence of Ziegler catalysts, cis,trans,trans-1,5,9-cyclododecatriene, cis,cis,trans-1,5,9-cyclododecatriene and all-trans-1,5,9-cyclododecatriene, as described, for example, in H. Weber et al. "Zur Bildungsweise von cis,trans,trans-Cyclododecatrien-(1.5.9) mittels titanhaltiger Katalysatoren" ins Liebigs Ann. Chem. 681 (1965) pp. 10-20. Cyclododecatriene can be prepared by trimerization of 1,3-butadiene using a titanium catalyst.

While all suitable titanium catalysts can in principle be used for the trimerization, the titanium tetrachloride/ethylaluminum sesquichloride catalyst described in the article by Weber et al. is particularly suitable.

The butadiene used for the trimerization particularly preferably has a purity determined by gas chromatography of at least 99.6% and more preferably at least 99.65%. Particularly preferably, the 1,3-butadiene used comprises no 1,2-butadiene and no 2-butyne within the detection limits.

This trimerization generally gives mixtures comprising at least 95% by weight, preferably at least 96% by weight and more preferably at least 97% by weight, of cis,trans,trans-1,5,9-cyclododecatriene. For example, the mixtures particularly preferably comprise about 98% by weight of cis,trans,trans-1,5,9-cyclododecatriene.

This cis,trans,trans-1,5,9-cyclododecatriene-comprising mixture can be used as such for the reaction in step (a2). It is likewise possible to separate off the cis,trans,trans-1,5,9-cyclododecatriene from the mixture by at least one suitable method, for example preferably by means of at least one distillation, and use it in the reaction in step (a2).

The oxidation in step (a2) can be carried out by all suitable methods known to those skilled in the art. The oxidation in step (a2) of the process of the invention is preferably carried out by means of dinitrogen monoxide.

In step (a2), cyclododecatriene is oxidized, preferably by reaction with dinitrogen monoxide. The reaction of the cyclododecatriene with dinitrogen monoxide can be carried out using at least one suitable solvent or diluent. Possible solvents or diluents are, inter alia, cyclododecane or cyclododecanone or saturated aliphatic or aromatic, optionally alkyl-substituted hydrocarbons. Essentially all customary solvents and/or diluents are suitable provided that they have neither a C—C double bond nor a C—C triple bond nor an aldehyde group.

In general, the addition of a solvent or diluent is not necessary in the reaction of cyclododecatriene with dinitrogen monoxide.

The temperatures in the reaction of cyclododecatriene with dinitrogen monoxide are preferably in the range from 140 to 350° C., more preferably in the range from 180 to 320° C. and particularly preferably in the range from 200 to 300° C.

It is possible to carry out the reaction of cyclododecatriene with dinitrogen monoxide at two or more temperatures or in two or more temperature ranges which are each within the limits indicated above. Temperature changes during the course of the reaction can be brought about continuously or discontinuously.

The pressures in the reaction of cyclododecatriene with dinitrogen monoxide are preferably greater than the autogeneous pressure of the starting material mixture or product mixture at the reaction temperature selected or the reaction temperatures selected. The pressures are preferably in the range from 1 to 1000 bar, more preferably in the range from 40 to 300 bar and particularly preferably in the range from 50 to 200 bar.

It is possible to carry out the reaction of cyclododecatriene with dinitrogen monoxide at two or more pressures or in two or more pressure ranges which are each within the limits indicated above. Pressure changes during the course of the reaction can be brought about continuously or discontinuously.

The reactors which can be used for the reaction of cyclododecatriene with dinitrogen monoxide are not subject to any particular restrictions. In particular, the reaction can be carried out batchwise or continuously. Accordingly, it is possible to use, for example, at least one CSTR (continuous stirred tank reactor) having at least one internal and/or at least one external heat exchanger, at least one tube reactor or at least one loop reactor as reactors. It is likewise possible to configure at least one of these reactors so that it has at least two different zones. Such zones can, for example, differ in terms of the reaction conditions, for example the temperature or the pressure, and/or in terms of the geometry of the zones, for example the volume or the cross section. If the reaction is carried out in two or more reactors, it is possible to use two or more identical types of reactor or at least two different types of reactor.

The reaction of cyclododecatriene with dinitrogen monoxide is preferably carried out in a single reactor. For example, the reaction is preferably carried out continuously.

The residence time of the reaction mixture in the at least one reactor in the reaction of cyclododecatriene with dinitrogen monoxide is generally in the range up to 20 hours, preferably in the range from 0.1 to 20 hours, more preferably in the range from 0.2 to 15 hours and particularly preferably in the range from 0.25 to 10 hours.

The molar ratio of dinitrogen monoxide to cyclododecatriene in the feed fed to the reaction of dinitrogen monoxide with cyclododecatriene is generally in the range from 0.05 to 4, preferably in the range from 0.06 to 1, more preferably in the range from 0.07 to 0.5 and particularly preferably in the range from 0.1 to 0.4.

The reaction of cyclododecatriene with dinitrogen monoxide can be carried out so that, at a very high selectivity to cyclododecadienone, a conversion of cyclododecatriene in the range up to 50%, preferably in the range from 5 to 30% and particularly preferably in the range from 10 to 20%, is achieved. The selectivity based on cyclododecadienone is generally at least 90%, preferably at least 92.5% and particularly preferably at least 95%.

It is in principle possible for any cyclododecatriene or any mixture of two or more different cyclododecatrienes to be reacted with dinitrogen monoxide. Mention may be made by way of example of, inter alia, 1,5,9-cyclododecatrienes, for example cis,trans,trans-1,5,9-cyclododecatriene or cis,cis,trans-1,5,9-cyclododecatriene or all-trans-1,5,9-cyclododecatriene.

Preference is given to using cis,trans,trans-1,5,9-cyclododecatriene as cyclododecatriene.

In general, the reaction of cis,trans,trans-1,5,9-cyclododecatriene with dinitrogen monoxide results in a cyclododeca-4,8-dienone isomer mixture which comprises at least two of the isomers cis,trans-cyclododeca-4,8-dienone, trans,cis-cyclododeca-4,8-dienone and trans,trans-cyclododeca-4,8-dienone. Accordingly, a typical isomer mixture comprises, for example, the isomers in molar ratios of about 1:1:0.08. This isomer mixture can be comprised in the composition (I) used in the process of the invention.

The reaction of cyclododecatriene with dinitrogen monoxide can in principle be carried out in the presence of a catalyst, but also without addition of a catalyst.

It is possible to use all suitable catalysts for the hydrogenation in step (a3). In particular, it is possible to use at least one homogeneous catalyst or at least one heterogeneous catalyst or both at least one homogeneous catalyst and at least one heterogeneous catalyst.

The catalysts which can be used preferably comprise at least one metal of transition group 7, 8, 9, 10 or 11 of the Periodic Table of the Elements. The catalysts which can be used according to the invention more preferably comprise at least one element selected from the group consisting of Re, Fe, Ru, Co, Rh, Ir, Ni, Pd, Pt, Cu and Au. Particularly preferably, the catalysts which can be used according to the invention comprise at least one element selected from the group consisting of Fe, Ni, Pd, Pt and Cu. The catalysts which can be used according to the invention particularly preferably comprise Pd, Pt, Ru or Ni.

Suitable catalysts are, for example, homogeneous catalysts comprising at least one element of transition group 8, 9 or 10. Further preference is given to homogeneous catalysts comprising Ru, Rh, Ir and/or Ni. Examples which may be mentioned here are $RhCl(TTP)_3$ and $Ru_4H_4(CO)_{12}$. Particular preference is given to homogeneous catalysts comprising Ru. For example, use is made of homogeneous catalysts as are described in U.S. Pat. No. 5,180,870, U.S. Pat. No. 5,321,176, U.S. Pat. No. 5,177,278, U.S. Pat. No. 3,804,914, U.S. Pat. No. 5,210,349, U.S. Pat. No. 5,128,296, and in D. R. Fahey in J. Org. Chem. 38 (1973), pp. 80-87, whose relevant disclosure is fully incorporated by reference into the present patent application. Such catalysts are, for instance, $(TPP)_2(CO)_3Ru$, $[Ru(CO)_4]_3$, $(TPP)_2Ru(CO)_2Cl_2$, $(TPP)_3(CO)RuH_2$, $(TPP)_2(CO)_2RuH_2$, $(TPP)_2(CO)_2RuClH$ or $(TPP)_3(CO)RuCl_2$.

It is possible to employ, in particular, at least one heterogeneous catalyst comprising at least one of the abovementioned metals as metal either as such, as a Raney catalyst and/or applied to a customary support. Preferred support materials are, for instance, activated carbons or oxides such as aluminum oxides, silicon oxides, titanium oxides or zirconium oxides. Mention may likewise be made of, inter alia, bentonites as support materials. If two or more metals are used, these can be present either separately or as an alloy. Here, it is possible to use at least one metal as such and at least one other metal as Raney catalyst or at least one metal as such and at least one other metal applied to at least one support, or at least one metal as Raney catalyst and at least one other metal applied to at least one support or at least one metal as such and at least one other metal as Raney catalyst and at least one other metal applied to at least one support.

The catalysts used can, for example, also be precipitated catalysts. Such catalysts can be reproduced by precipitating their catalytically active components from salt solutions thereof, in particular from solutions of nitrides and/or acetates thereof, for example by addition of solutions of alkali metal and/or alkaline earth metal hydroxides and/or carbonate, for example sparingly soluble hydroxides, hydrated oxides, basic salts or carbonates, subsequently drying the precipitates obtained and then converting these by calcination at generally from 300 to 700° C., in particular from 400 to 600° C., into the corresponding oxides, mixed oxides and/or mixed-valence oxides which are reduced to the respective metals and/or oxidic compounds in a lower oxidation state and converted into the actual catalytically active form by treatment with hydrogen or hydrogen-comprising gases at temperatures of generally from 50 to 700° C., in particular from 100 to 400° C. In general, reduction is continued until no more water is formed. In the production of precipitated catalysts comprising a support material, the precipitation of the catalytically active components can be carried out in the presence of the appropriate support material. The catalytically active components can advantageously be precipitated from the corresponding salt solutions simultaneously with the support material.

Preference is given to using hydrogenation catalysts which comprise the metals or metal compounds which catalyze the hydrogenation deposited on a support material.

Apart from the abovementioned precipitated catalysts which comprise a support material in addition to the catalytically active components, support materials in which the hydrogenatively active catalytic component has been applied to a support material by, for example, impregnation are generally also suitable for the process of the invention.

The way in which the catalytically active metal is applied to the support is generally not critical and the application can be effected in a variety of ways. The catalytically active metals can, for example, be applied to these support materials by impregnation with solutions or suspensions of the salts or oxides of the respective elements, drying and subsequent reduction of the metal compounds to form the respective metals or compounds in a lower oxidation state by means of a reducing agent, preferably by means of hydrogen or complex hydrides. Another possible way of applying the catalytically active metals to these supports is to impregnate the supports with solutions of salts which are easily decomposed thermally, for example nitrates, or complexes which are easily decomposed thermally, for example carbonyl or hydride complexes, of the catalytically active metals and to heat the support which has been impregnated in this way to temperatures in the range from 300 to 600° C. in order to decompose the adsorbed metal compounds thermally. This thermal decomposition is preferably carried out under a protective gas atmosphere. Suitable protective gases are, for example nitrogen, carbon dioxide, hydrogen or the noble gases. Furthermore, the catalytically active metals can be deposited on the catalyst support by vapor deposition or by flame spraying. The amount of the catalytically active metals present in these supported catalysts is in principle not critical for the success of the process of the invention. In general, higher contents of catalytically active metals in these supported catalysts lead to higher space-time conversions than do lower contents. In general, use is made of supported catalysts whose content of catalytically active metals is in the range from 0.1 to 90% by weight, preferably in the range from 0.5 to 40% by weight, based on the total weight of the catalyst. Since these contents are based on the total catalyst including support material but the various support materials have very different specific gravities and specific surface areas, it is also conceivable for these contents to be below or above these values without this having a disadvantageous effect on the success of the process of the invention. Of course, it is also possible for a plurality of the catalytically active metals to be applied to the respective support material. Furthermore, the catalytically active metals can be applied to the support by, for example, the process of DE-A 25 19 817, EP 1 477 219 A1 or EP 0 285 420 A1. In the catalysts according to the abovementioned documents, the catalytically active metals are present as alloys which are produced by thermal treatment and/or reduction of the catalyst precursors obtained, for example, by impregnation of the support material with a salt or complex of the abovementioned metals.

The activation of both the precipitated catalysts and the supported catalysts can also be carried out in situ at the beginning of the reaction by means of the hydrogen present. Preference is given to separately activating these catalysts before use.

As support materials, it is generally possible to use the oxides of aluminum and titanium, zirconium dioxide, silicon dioxide, clay minerals such as montmorillonites, silicates such as magnesium or aluminum silicates, zeolites such as the structure types ZSM-5 or ZSM-10, or activated carbon. Preferred support materials are aluminum oxides, titanium dioxide, silicon dioxide, zirconium dioxide and activated carbon. Of course, it is also possible to use mixtures of various support materials as support for catalysts which can be used in the process of the invention.

For the purposes of the invention, very particularly preferred catalysts are ones which comprise Ni, Pt and/or Pd and have been applied to a support. Very particularly preferred supports are or comprise activated carbon, aluminum oxide, titanium dioxide and/or silicon dioxide.

The at least one heterogeneous catalyst can, for example, be used as a suspended catalyst or as a fixed-bed catalyst.

If, for example, the hydrogenation in step (a3) of the process of the invention is carried out using at least one suspended catalyst, the hydrogenation is preferably carried out in at least one stirred reactor or in at least one bubble column or in at least one packed bubble column or in a combination of two or more identical or different reactors.

The term "different reactors" in the present context refers both to different types of reactor and to reactors of the same type which differ, for example, in terms of their geometry, for example their volume and/or their cross section, and/or in terms of the hydrogenation conditions in the reactors.

If, for example, the hydrogenation in step (a3) of the process of the invention is carried out using at least one fixed-bed catalyst, preference is given to using at least one tube reactor such as at least one shaft reactor and/or at least one shell-and-tube reactor, with a single reactor being able to be operated in the upflow mode or the downflow mode. If two or more reactors are used, at least one can be operated in the upflow mode and at least one can be operated in the downflow mode.

If, for example, a heterogeneous catalyst is used as suspended catalyst in the hydrogenation, this is, for the purposes of the present invention, preferably separated off by means of at least one filtration step. The catalyst which has been separated off in this way can be recirculated to the hydrogenation or passed to at least one other desired process. It is likewise possible to work up the catalyst, for example in order to recover the metal comprised in the catalyst.

If, for example, a homogeneous catalyst is used as catalyst in the hydrogenation in step (a3), this is preferably separated off by means of at least one distillation step for the purposes of the present invention. In this distillation, it is possible to use one or two or more distillation columns. The catalyst which has been separated off in this way can be recirculated to the hydrogenation or be passed to at least one other desired process. It is likewise possible to work up the catalyst, for example in order to recover the metal comprised in the catalyst.

Before use in a desired process, for example before recirculation to the process of the invention, both the at least one homogeneous catalyst and the at least one heterogeneous catalyst can, should this be necessary, be regenerated by means of at least one suitable process.

In the reactor used according to the invention, the heat can be removed internally, for example by means of cooling coils, and/or externally, for example by means of at least one heat exchanger. If, for example, at least one tube reactor is preferably used for the hydrogenation, the reaction is preferably operated with circulation via an external circuit into which the heat removal is integrated.

If, in a preferred embodiment of the process of the invention, the hydrogenation is carried out continuously, use is more preferably made of at least two reactors, more preferably at least two tube reactors, more preferably at least two tube reactors connected in series and particularly preferably precisely two tube reactors connected in series. The hydrogenation conditions in the reactors used can be identical or different and are each within the above-described ranges.

If the hydrogenation in step (a3) is carried out over at least one suspended catalyst, the residence time is generally in the range from 0.05 to 50 hours, for example in the range from 0.5 to 50 hours, preferably in the range from 1 to 30 hours and particularly preferably in the range from 1.5 to 25 hours, very particularly preferably in the range from 1.5 to 10 hours. It is immaterial whether a main reactor and an after-reactor or additionally further reactors are used for the purposes of the invention. For all of these embodiments, the total residence time is within the ranges indicated above.

If the hydrogenation in the process of the invention is carried out continuously over at least one fixed-bed catalyst, the space velocity over the catalyst (kg of feed/liter of catalyst×h) is generally in the range from 0.03 to 20, preferably in the range from 0.05 to 5 and particularly preferably in the range from 0.1 to 2. It is immaterial whether a main reactor and an after-reactor or additionally further reactors are used for the purposes of the invention. For all these embodiments, the total space velocity is within the ranges indicated above.

In general, the hydrogenation temperature in the main reactor is in the range from 0 to 350° C., preferably in the range from 20 to 300° C., more preferably in the range from 50 to 250° C. and particularly preferably in the range from 80 to 220° C.

In the hydrogenation according to the invention, the hydrogen pressure in the main reactor is generally in the range from 1 to 325 bar, preferably in the range from 5 to 300 bar, more preferably in the range from 10 to 250 bar and particularly preferably in the range from 15 to 150 bar.

At least one suitable solvent or diluent can be used in the hydrogenation according to the invention in step (a3). Suitable solvents or diluents are in principle all solvents and diluents which are not hydrogenated or reacted in another way under the hydrogenation conditions, e.g. alcohols, ethers, hydrocarbons, water, aromatics or ketones, in particular toluene or cyclododecane.

In a preferred embodiment of the process of the invention, the hydrogenation in step (a3) is carried out without addition of a solvent or diluent.

In a further embodiment, the composition (I') can be obtained by trimerization of butadiene to form cyclododecatriene, hydrogenation of cyclododecatriene to form cyclododecane and subsequent oxidation of cyclododecane to form cyclododecanone.

In a further embodiment, the present invention therefore also provides a process as described above for preparing cyclododecanone, wherein step (a) comprises at least the steps
- (a-I) trimerization of butadiene to form cyclododecatriene,
- (a-II) hydrogenation of cyclododecatriene to form cyclododecane,
- (a-III) oxidation of cyclododecane to form cyclododecanone.

According to the invention, further treatments, for example purification steps, can be carried out between steps (a-I), (a-II) and (a-III). The statements made above in respect of step (a1) apply to step (a-I). As regards step (a-II) and step (a-III), reference is made to DE 103 44 594 A, whose relevant contents are fully incorporated by reference into the present patent application.

It is likewise possible, for the purposes of the present invention, for cyclododecanone to be obtained by trimerization of butadiene to form cyclododecatriene, oxidation of cyclododecatriene to form cyclododecatriene epoxide and subsequent hydrogenation and rearrangement of cyclododecatriene epoxide to form cyclododecanone.

In a further embodiment, the present invention also provides a process as described above for preparing cyclododecanone, wherein step (a) comprises at least the steps
- (a-A) trimerization of butadiene to form cyclododecatriene,
- (a-B) oxidation of cyclododecatriene to form cyclododecatriene epoxide,
- (a-C) hydrogenation of cyclododecatriene epoxide and rearrangement to form cyclododecanone.

According to the invention, further treatments, for example purification steps, can be carried out between steps (a-A), (a-B) and (a-C). The statements made above in respect of step (a1) apply to step (a-A). As regards step (a-B) and step (a-C), reference is made to EP 1 018 498 B1, whose relevant contents are fully incorporated by reference into the present patent application.

It is likewise possible, for the purposes of the present invention, for cyclododecanone to be obtained by trimerization of butadiene to form cyclododecatriene, selective hydrogenation of cyclododecatriene to form cyclododecene and subsequent oxidation of cyclododecene to form cyclododecanone.

In a further embodiment, the present invention also provides a process as described above for preparing cyclododecanone, wherein step (a) comprises at least the steps
- (a-α) trimerization of butadiene to form cyclododecatriene,
- (a-β) selective hydrogenation of cyclododecatriene to form cyclododecene,
- (a-γ) oxidation of cyclododecene to form cyclododecanone.

According to the invention, further treatments, for example purification steps, can be carried out between steps (a-α), (a-β) and (a-γ). The statements made above in respect of step (a1) apply to step (a-α). As regards step (a-β) and step (a-γ), reference is made to DE 103 44 594 A1, whose relevant contents are fully incorporated by reference into the present patent application.

According to a further aspect, the present invention relates to the use of at least one catalyst comprising at least one transition metal for purifying a composition (1) comprising at least one cyclic ketone. As described above, the thermal treatment with a catalyst comprising at least one transition metal makes it possible to separate off impurities, in particular organic oxygen-comprising compounds whose number of carbon atoms is similar or identical to that of the cyclic ketone comprised in the composition (I), more easily.

The present invention therefore provides for the use of a catalyst comprising at least one transition metal for purifying a composition (1) comprising at least one cyclic ketone having from 7 to 16 carbon atoms by thermal treatment of the composition (I) with a catalyst comprising at least one transition metal.

In particular, the present invention also provides, in a preferred embodiment, for a use as described above of at least one catalyst comprising at least one transition metal for purifying a composition (I) comprising at least one cyclic ketone having from 7 to 16 carbon atoms, wherein the cyclic ketone is cyclododecanone.

In a preferred embodiment, the invention provides for the use of a heterogeneous catalyst comprising at least one transition metal in an amount of from 1 to 10% by weight, based on the cyclic ketone, for purifying a composition comprising at least one cyclic ketone having from 7 to 16 carbon atoms.

In particular, the process of the invention gives pure products at high catalyst operating lives and can be carried out simply. The apparatus required for the process of the invention is also simple and inexpensive.

The invention is illustrated below by means of examples.

EXAMPLES

The contents reported in the examples are percent by area determined by gas chromatography (GC method)

Example 1

A crude cyclododecanone product prepared by the process as described in DE 103 44 595 A using a cyclododecadienone having a purity of about 97.5% in the hydrogenation step comprises 97% of cyclododecanone and many further components, namely 0.2% of cyclododecane, 0.5% of cyclododecanol, 0.6% of dodecanol, 0.3% of dodecanal, 0.6% of hydroxymethylcycloundecane, 0.1% of formylcycloundecane and 0.2% of many further products whose individual contents are each below 0.05%. This crude cyclododecanone product is reacted over 100 ml of an Ru (5%) on titanium dioxide at 220° C. and a space velocity over the catalyst of 0.5 kg of feed per liter of catalyst×h. After a period of operation of 24 hours, the reaction product mixture collected is subsequently fractionally distilled at 5 mbar in a column. This gives cyclododecanone having purities of >99.8% in a distillation yield of about 97%.

Comparative Example 1

Crude cyclododecanone product is worked up by a method analogous to example 1 but without the treatment with catalyst. This gives cyclododecanone having purities of from 99.3 to 99.5% in a distillation yield of about 60%. The remaining fractions comprise cyclododecanone having purities of from 60 to 99.3%.

The invention claimed is:

1. A process for preparing cyclododecanone which comprises at least the steps
    (a) preparing of a composition (I') comprising at least cyclododecanone, comprising at least the steps
    (a-1) trimerization of a butadiene to form a cyclododecatriene,
    (a-2) oxidating the cyclododecatriene to form a cyclododecadienone,
    (a-3) hydrogenating the cyclododecadienone to form the cyclododecanone,
    (b) purifying the composition (I'), which comprises at least the steps
        (i) thermal treating of the composition (I') with at least one catalyst comprising at least one transition metal,
        (ii) further purifying by means of a process selected from the group consisting of distillation, extraction and crystallization.

2. The process according to claim 1, wherein the treating in step (i) is carried out at a temperature of from 60 to 350° C.

3. The process according to claim 1, wherein the treating in step (i) is carried out for a time of from 0.1 to 50 hours.

4. The process according to claim 2, wherein the treatment in step (i) is carried out for a time of from 0.1 to 50 hours.

5. The process according to claim 1, wherein the catalyst is present in homogeneously dissolved form or heterogeneous form.

6. The process according to claim 4, wherein the catalyst is present in homogeneously dissolved form or heterogeneous form.

7. The process according to claim 1, wherein the composition (I') further comprises at least one further oxygen-comprising organic compound in addition to the at least one cyclic ketone.

8. The process according to claim 6, wherein the composition (I') further comprises at least one further oxygen-comprising organic compound in addition to the at least one cyclic ketone.

9. A process for preparing cyclododecanone which comprises at least the steps
    (a) preparing of a composition (I') comprising at least cyclododecanone, comprising at least the steps
    (a-1) trimerization of a butadiene to form a cyclododecatriene,
    (a-2) oxidating the cyclododecatriene to form a cyclododecadienone,
    (a-3) hydrogenating the cyclododecadienone to form the cyclododecanone,
    (b) purifying the composition (I'), which comprises at least the steps
        (i) thermal treating of the composition (I') with at least one catalyst comprising at least one transition metal,
        (ii) further purifying by means of a process selected from the group consisting of distillation, extraction and crystallization
    wherein the treating in step (i) is carried out at a temperature of from 60 to 350° C. and for a time of from 0.1 to 50 hours.

10. A process for preparing cyclododecanone which comprises at least the steps
    (a) preparation of a composition (I') comprising at least cyclododecanone, comprising at least the steps
    (a-1) trimerization of a butadiene to form a cyclododecatriene,
    (a-2) oxidating the cyclododecatriene to form a cyclododecadienone,
    (a-3) hydrogenating the cyclododecadienone to form the cyclododecanone,
    (b) purifying the composition (I'), which comprises at least the steps
        (i) thermal treating the composition (I') with at least one catalyst comprising at least one transition metal,
        (ii) further purifying by means of a process selected from the group consisting of distillation, extraction and crystallization,
    wherein the treating in step (i) is carried out at a temperature of from 60 to 350° C. and for a time of from 0.1 to 50 hours, and
    wherein the composition (I') comprises at least one further oxygen-comprising organic compound in addition to the at least one cyclic ketone.

11. The process as claimed in claim 1, wherein the process in step (b)(ii) is crystallization or extraction.

12. The process as claimed in claim 1, wherein the process in step (b)(ii) is crystallization.

13. The process as claimed in claim 1, wherein the process in step (b)(ii) is extraction.

14. The process as claimed in claim 1, wherein the process in step (b)(ii) is distillation.

15. The process as claimed in claim 10, wherein the process in step (b)(ii) is crystallization or extraction.

16. The process as claimed in claim 10, wherein the process in step (b)(ii) is crystallization.

17. The process as claimed in claim 10, wherein the process in step (b)(ii) is extraction.

18. The process as claimed in claim 10, wherein the process in step (b)(ii) is distillation.

* * * * *